United States Patent

Jakob et al.

[11] Patent Number: 5,269,887
[45] Date of Patent: Dec. 14, 1993

[54] PROCESS FOR THE PURIFICATION OF BISPHENOLS

[75] Inventors: Wolfgang Jakob, Moers; Manfred Schmidt, Krefeld; Dieter Freitag, Krefeld; Klaus D. Berg, Krefeld, all of Fed. Rep. of Germany

[73] Assignee: Bayer Aktiengesellschaft, Leverkusen, Fed. Rep. of Germany

[21] Appl. No.: 833,105

[22] Filed: Feb. 10, 1992

[30] Foreign Application Priority Data

Feb. 21, 1991 [DE] Fed. Rep. of Germany ....... 4105428

[51] Int. Cl.$^5$ ..................... B01D 3/10; C07C 37/74
[52] U.S. Cl. ..................... 203/91; 159/47.1; 568/724
[58] Field of Search .......... 203/91; 202/205; 568/724, 749; 159/47.1; 23/294 R

[56] References Cited

U.S. PATENT DOCUMENTS

| | | | |
|---|---|---|---|
| 2,324,300 | 7/1943 | Harvey | 568/724 |
| 2,791,616 | 5/1957 | Luten, Jr. | 568/727 |
| 2,936,267 | 5/1960 | Farmholz et al. | 203/63 |
| 3,207,795 | 9/1965 | Prahl et al. | 568/724 |
| 3,936,507 | 2/1976 | Ligorati et al. | 568/724 |
| 4,026,761 | 5/1977 | Vargiu et al. | 159/DIG. 15 |
| 4,201,878 | 5/1980 | Mark et al. | 568/723 |
| 4,294,994 | 10/1981 | Li | 568/724 |
| 4,354,046 | 10/1982 | Ladewig et al. | 568/724 |
| 4,400,553 | 8/1983 | Aneja | 210/806 |
| 4,447,655 | 5/1984 | Mendiratta | 568/724 |
| 4,533,764 | 8/1985 | Chang et al. | 568/724 |
| 4,740,635 | 4/1988 | Gomes de Matos et al. | 568/724 |
| 4,902,836 | 2/1990 | Kissinger | 568/724 |
| 4,946,877 | 8/1990 | Imuro et al. | 568/728 |
| 4,950,806 | 8/1990 | Limuro et al. | 568/724 |
| 4,954,661 | 9/1990 | Limuro et al. | 568/728 |
| 5,091,058 | 2/1992 | Davie | 203/91 |

FOREIGN PATENT DOCUMENTS

| | | | |
|---|---|---|---|
| 0330146 | 8/1989 | European Pat. Off. | 568/724 |
| 422428 | 2/1942 | Japan | 568/728 |
| 1052618 | 12/1966 | United Kingdom | 568/728 |
| 8000150 | 2/1980 | World Int. Prop. O. | 568/724 |

*Primary Examiner*—Virginia Manoharan
*Attorney, Agent, or Firm*—Connolly & Hutz

[57] ABSTRACT

A process for the purification of bisphenols by distillation.

3 Claims, No Drawings

PROCESS FOR THE PURIFICATION OF BISPHENOLS

This invention relates to a process for the purification of bisphenols by distillation.

It is well known that bisphenols are prepared from, for example, ketones and phenols in the presence of catalysts (e.g. BE-PS 738 962, JP-A 62/178 534, GB-A 21 108).

After the reaction, the bisphenol obtained may separate as a 1:1 adduct with the phenol used. This adduct (mixed crystal) may be washed with the phenol for further purification. The phenol may be extracted with solvents to separate the components of the mixed crystals (e.g. GB-A 21108; JP-A 017 588) or the mixed crystal may be melted and the phenol distilled from the melt at an elevated temperature (e.g. JP-A 15 337). The extract must then be worked up by an elaborate process for obtaining the phenol. Removal of the phenol from the mixed crystals by distillation at a high temperature above the melting point of the mixed crystals may have its disadvantages, e.g. with respect to the bisphenol produced.

It has now been found that removal of the phenol from the bisphenol/phenol adducts obtained in the known processes for the preparation of bisphenols can be carried out below the melting point of the bisphenol/phenol adduct (mixed crystal) at reduced pressure.

The present invention therefore relates to a process for the purification of bisphenols obtained as bisphenol/phenol adducts in known processes for their preparation from ketones and phenols, characterised in that the phenol is removed at reduced pressure at temperatures below the melting point of the bisphenol/phenol adduct.

According to the invention, bisphenols corresponding to formula (I)

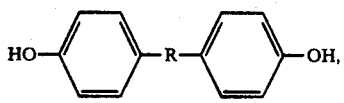

wherein
R stands for $C_1$–$C_{10}$-alkylene or $C_5$–$C_{15}$-cycloalkylene may advantageously be used.

The following are examples of particularly preferred bisphenols: Bisphenol A (2,2-bis[-4-hydroxyphenyl]propane), bisphenol TMC (1,1-bis-[4-hydroxyphenyl]-3,3,5-trimethylcyclohexane), bisphenol Z (1,1-bis-(4-hydroxy-phenyl)-cyclohexane) and bisphenol-3M (1,1-bis-(hydroxy-phenyl)-3-methylcyclohexane).

The bisphenol/phenol adducts (mixed crystals) contain from 0.1 to 2.15 mol of phenol per mol of bisphenol.

The mixed crystals are preferably in the form of about 1:1 adducts of bisphenol/phenol.

According to the invention, separation of the components of the mixed crystals is carried out in the solid phase at temperatures below their melting point. The temperatures employed for this separation are preferably in the range of from 50° C. to 200° C., preferably from 90° C. to 120° C. The separation temperature is preferably 10 degrees Centigrade below the melting point of the given mixed crystal in the stated temperature ranges.

The separation according to the invention (in which the phenol is removed by sublimation and the bisphenol is left behind) is preferably carried out without solvent at a pressure of from 0.5 to 100 mbar, preferably from 0.5–15 mbar.

Conventional driers such as plate driers, tumbler driers, paddle driers, cascade or spray driers, countercurrent driers, etc. are used for carrying out the purification according to the invention of the bisphenols (separation of the mixed crystals).

EXAMPLES

The examples summarized in Table 1, show that both the phenol split off in the solid phase mixed crystal cleavage and the bisphenol remaining behind can be of greater purity than the corresponding products obtained by cleavage above the melting point.

Solid phase drying was carried out in a conventional laboratory paddle drier and cleavage above the melting point was carried out in an ordinary laboratory distillation apparatus. The distillates and the residues were investigated gas chromatographically and/or their colour value was determined (Hazen colour value according to DIN 53 409).

EXPERIMENTAL METHOD

A) 100 g of the mixed crystals were heated to 180° C. under vacuum (18 mbar) in a 250 ml three-necked flask with bridge and receiver and maintained at 180° C. for 30 minutes, during which time the phenol distilled off.

B) 150 g of the mixed crystals were introduced into a paddle drier. The drier was adjusted to a vacuum of about 18 mbar and heated to the temperatures shown in the Table. The phenol distilled off.

The following were investigated:
1) Mixed crystals of phenol and 1,1-bis-(4-hydroxyphenyl)-cyclohexane (BP-Z*).
   * BP=bisphenol
2) Mixed crystals of phenol and 1,1-bis-(4-hydroxyphenyl)-3-methylcyclohexane (BP-3M*)
   * BP=bisphenol
3) Mixed crystals of phenol and 1,1-bis-(4-hydroxyphenyl)-3,3,5-trimethylcyclohexane (BP-TMC*)
   * BP=bisphenol
4) Mixed crystals of phenol and 2,2-bis-(4-hydroxyphenyl)-propane (BP-A)

TABLE 1

| Example No. | Product | T (°C.) | Pressure (mbar) | Time (min) | CV[1] (HV) | GC purity[2] (% by wt.) | Impurities[3] (% by wt.) |
|---|---|---|---|---|---|---|---|
| 1,A | BPZ | 190 | 20 | 30 | 15–20 | 95.0 | 0.6 |
|  | phenol |  |  |  |  | 98.7 | 0.05 |
| 1,B | BPZ | 130 | 20 | 270 | 40 | 99.3 | 0.04 |
|  | phenol |  |  |  |  | 98.3 | 0.01 |
| 2,A | BP3M | 190 | 20 | 30 | grey | 97.1 | 1.5 |
|  | phenol |  |  |  |  | 99.6 | 0.18 |
| 2,B | BP3M | 130 | 20 | 180 | 20–30 | 98.9 | 1.0 |

TABLE 1-continued

| Example No. | Product | T (°C.) | Pressure (mbar) | Time (min) | CV[1] (HV) | GC purity[2] (% by wt.) | Impurities[3] (% by wt.) |
|---|---|---|---|---|---|---|---|
| | phenol | | | | | 99.7 | 0.17 |
| 3,A | BPTMC | 190 | 20 | 30 | 200 | 95.3 | 3.5 |
| | phenol | | | | | 99.0 | 0.3 |
| 3,B | BPTMC | 130 | 20 | 240 | 40 | 99.9 | 0.01 |
| | phenol | | | | | 97.8 | 0.01 |
| 4,A | BPA | 190 | 20 | 30 | 20 | 99.1 | 0.9 |
| | phenol | | | | | 99.1 | 0.9 |
| 4,B | BPA | 90 | 20 | 180 | 15 | 99.7 | 0.3 |
| | phenol | | | | 90 | 99.9 | 0.1 |

[1] Colour value (CV) of the resulting bisphenol determined as Hazen Colour value DIN 53 409
[2] GC purity of the bisphenol or of the phenol distilled off
[3] other than bisphenol or phenol

We claim:

1. A process for the purification of bishphenols obtained as bisphenol/phenol adducts in known processes for their preparation from ketones and phenols, said bisphenol/phenol adducts containing from 0.1 to 2.15 mol of phenol per mol of bishphenol, wherein said process consists essentially of removing phenol from a bisphenol/phenol adduct at a reduced pressure of from about 0.5 to 100 mbar by distillation or sublimation of the bisphenol/phenol adduct in the solid phase at a temperature of about 10° C. below the melting point of the bisphenol/phenol adduct in the temperature range of from about 50°-200° C. wherein the removal of the phenol from the solid phase adduct directly results in the final purified bisphenol product.

2. A process according to claim 1, wherein said reduced rpessure is from about 0.5 to 15 mbar.

3. A process according to claim 1, wherein said temperature is from about 90° to 120° C.

* * * * *

UNITED STATES PATENT AND TRADEMARK OFFICE
CERTIFICATE OF CORRECTION

PATENT NO. : 5,269,887

DATED : December 14, 1993

INVENTOR(S) : Jakob, et al.

It is certified that error appears in the above-indentified patent and that said Letters Patent is hereby corrected as shown below:

On the cover page in section [56] "References cited", the following references should be added:

| U.S. Patent No. | 4,180,683 | 12/1979 | Mitchell | 568/724 |
| European Pat. Off. | 0343349 | 11/1989 | | |
| France | 2,073,717 | 10/1971 | | |
| European Pat. Off. | 0332203 | 9/1989 | | |
| European Pat. Off. | 0319326 | 6/1989 | | |

Column 3:
  Claim 1, line 1, the word "bishphenols" should be --bisphenols--.
Column 4:
  Claim 2, line 2, the word "rpessure" should be --pressure--.

Signed and Sealed this

Twenty-eighth Day of June, 1994

*Attest:*

BRUCE LEHMAN

*Attesting Officer*     *Commissioner of Patents and Trademarks*